United States Patent [19]
Hoyer et al.

[11] Patent Number: 5,304,496
[45] Date of Patent: Apr. 19, 1994

[54] BIOLOGICAL REGULATION OF MINERALIZATION

[75] Inventors: John Hoyer, Wynnewood, Pa.; John Sinclair; Leszek Borysiewicz, both of Cambridgeshire, United Kingdom

[73] Assignee: Children's Hospital of Philadelphia, Philadelphia, Pa.

[21] Appl. No.: 712,476

[22] Filed: Jun. 10, 1991

[51] Int. Cl.[5] .................... G01N 33/53; A61K 37/02; C07K 7/10; C07K 7/08
[52] U.S. Cl. ...................................... 436/86; 435/7.1; 514/8; 514/12; 514/14; 514/89.1; 530/324; 530/327; 530/350; 530/395; 530/834; 530/835; 530/840
[58] Field of Search ............... 530/350, 395, 834, 835, 530/840, 324, 327; 514/8, 12, 14, 891; 436/86; 435/7.1

[56] References Cited

U.S. PATENT DOCUMENTS

| | | | |
|---|---|---|---|
| 4,828,821 | 5/1989 | Kelley | 424/49 |
| 5,049,659 | 9/1991 | Cantor et al. | 530/351 |

OTHER PUBLICATIONS

*Affinity Chromatography: A Practical Approach*, P. D. Dean, W. S. Johnson, and F. A. Middle, eds. (IRL Press, Washington, D.C., 1985).
*Antibodies: A Laboratory Manual* (Cold Springs Harbor Laboratory Press, N.Y,. 1989).
Clayman et al., *J. Exp. Med.*, vol. 161, pp. 290–305 (1985).
Coe et al., *Kidney Int.*, vol. 38, pp. 625–631 (1990).
Craig et al., *J. Biol. Chem.*, vol. 264, pp. 9682–9689 (1989).
Fisher et al., *J. Biol. Chem.*, vol. 262, pp. 9702–9708 (1987).
Houghton, *Proc. Natl. Acad. Sci. USA*, vol. 82, pp. 5131–5135 (1985).
Kiefer et al., *Nucleic Acids Res.*, vol. 17, pp. 3306–3308 (1989).
Kubota et al., *Biochem. Biophys. Res. Cumm.*, vol. 162, pp. 1453–1459 (1989).
Laemmli, *Nature*, vol. 227, pp. 68–685 (1970).
Lian et al., *J. Clin. Invest.*, vol. 59, pp. 1151–1157 (1977).
Miyazaki et al., *Nucleic Acids Res.*, vol. 17, pp. 3298–3298 (1989).
Nakagawa et al., *J. Biol. Chem.*, vol. 258, pp. 12594–12600 (1983).
Nakagawa et al., *J. Clin. Invest.*, vol. 79, pp. 1782–1787 (1987).
Oldberg et al., *Proc. Natl. Acad. Sci. USA*, vol. 83, pp. 8819–8823 (1986).
Patarca et al., *J. Exp. Med.*, vol. 170, pp. 145–161 (1989).
Prince et al., *J. Biol. Chem.*, vol. 262, pp. 2900–2907 (1987) 8823 (1986).
Przysiecki et al, *Proc. Natl. Acad. Sci. USA*, vol. 84, pp. 7858–7860 (1987).
Senger et al., *Cancer Research*, vol. 48, pp. 5770–5774 (1988).
Senger et al., *Biochem. Biophys. Acta*, vol. 996, pp. 43–48 (1989).
Singh et al., *J. Exp. Med.*, vol. 171, pp. 1931–1942 (1990).

(List continued on next page.)

*Primary Examiner*—Robert A. Wax
*Assistant Examiner*—Rebecca Prouty
*Attorney, Agent, or Firm*—Woodcock Washburn Kurtz Mackiewicz & Norris

[57] ABSTRACT

An aspartic acid rich protein isolated from human urine, as well as proteins having substantial homology thereto and active portions of the foregoing are effective modulators of mineralization in mammals. These proteins and peptides are useful as therapeutic agents, such as in the treatment of kidney stone disease. Hybridoma cell lines capable of producing monoclonal antibodies to these proteins and peptides and monoclonal antibodies produced by these hybridomas are disclosed. These monoclonal antibodies are also useful as therapeutic agents, such as in the treatment of osteoporosis, and further have utility as diagnostic agents. Other uses are also described.

10 Claims, 6 Drawing Sheets

OTHER PUBLICATIONS

Spector et al., *Invest. Urol.*, vol. 13, pp. 387–389 (1976).
Tamm et al., *Proc. Soc. Exp. Biol. Med.*, vol. 74, pp. 108–114 (1950).
Towbin et al., *Proc. Natl. Acad. Sci. USA*, vol. 76, pp. 4350–4354 (1979).
Worcester et al., *Am. J. Physiol.*, 255, F1197–F1205 (1988).
Wrana et al., *Nucleic Acids Res.*, vol. 17, pp. 10119–10119 (1989).
Yoshioka et al., *J. Clin. Invest.*, vol. 82, pp. 1614–2623 (1988).
Young et al, *Genomics*, vol. 7, pp. 491–502 (1990).
Butler, *Connective Tissue Research*, vol. 23, pp. 123–136 (1989).
Shiraga et al., *Pediatric Nephrology*, vol. 3, p. C198 (1989) (abstract).
Garvey et al., *Methods in Immunology: A Laboratory Text for Instruction and Research*, 3rd ed., Chs. 22, 24–30, W. A. Benjamin Inc. (Reading Mass. 1977).
*Remington's Pharmaceutical Sciences*, Gennaro, A. R., ed., Part 8, Mack Publishing Co., Easton, Pa. (1985).
Termine et al., *Calcif. Tissue Int.*, vol. 31, pp. 247–251 (1980).
Shiraga et al., *Kidney International*, vol. 35, p. 363 (1989) (abstract).
Ligabue et al., *Clin. Chim. Acta*, vol. 98, pp. 39–46 (1979).
Meyer et al., *Invest. Urol.*, vol. 13, pp. 36–39 (1975).
Maniatis, Fritsch & Sambrook, *Molecualr Cloning: A Laboratory Manual*, vols. 1–3, 2nd ed. (Cold Spring Harbor Laboratory Press, N.Y. 1989).
Craig et al., *Biochem. Biophys, Res. Commun.*, vol. 157, pp. 166–173 (1988).
Singh et al., *J. Biol. Chem.*, vol. 265, pp. 18696–18701 (1990).
Miyazaki et al., *J. Biol. Chem.*, vol. 265, pp. 14432–14438 (1990).
Yoon et al., *Biochem. Biophys. Res. Comm.*, vol. 148, pp. 1129–1136 (1987).
Nomura et al., *J. Cell Biol.*, vol. 106, pp. 441–450 (1988).
Mark et al., *Differentiation*, vol. 37, pp. 123–136 (1988).
Nagata et al., *Biochem. Biophys. Res. Comm.*, vol. 165, pp. 234–240 (1989).
Stein et al., *FASEBJ*, vol. 4, pp. 3111–3123 (1990).
Mark et al., *Cell Tissue Res.*, vol. 251, pp. 23–30 (1988).
Swanson et al. *Hear. Res.*, vol. 41, pp. 169–177 (1989).
Weiner et al., *Science*, vol. 190, pp. 987–989 (1975).
Weiner, *Amer. Zool.*, vol. 24, pp. 945–951 (1984).
Lee et al., *Biochem*, vol. 16, pp. 2971–2979 (1977).
Wheeler et al, *Science, vol. 212, pp. 1397–1398 (1981)*.
Addadi et al., *Proc. Natl. Acad. Sci. USA*, vol. 82, pp. 4110–4114 (1985).
Addadi et al., *Proc. Natl. Acad. Sci. USA*, vol. 84, pp. 2732–2736 (1987).
Berman et al., *Nature*, vol. 331, pp. 546–548 (1988).
Linde et al., *Calcif. Tissue Int.*, vol. 44, pp. 286–295 (1989).
Romberg et al., *Biochem.*, vol. 25, pp. 1176–1180 (1986)
Van deLoo et al, *Biochem. Biophys. Res. Comm.*, vol. 142, pp. 113—199 (1987).
Campbell et al., *Calcif. Tissue Int.*, vol. 45, pp. 122–128 (1989).
Prince et al., *Collagen Rel. Res.*, vol. 7, pp. 305–313 (1987).
Noda et al, *J. Cell Biol.*, vol. 108, pp. 713–718 (1989).
Noda et al, *Proc. Natl. Acad. Sci., USA*, vol. 87, pp. 9995–9999 (1990).
Reinholt et al., *Proc. Natl. Acad. Sci. USA*, vol. 87, pp. 4473–4475 (1990).

FIG. 3

```
HUP   1-22   V K Q A D S G S S E E K Q L Y N K Y P D A V
pHOP 19-40   V K Q A D S G S S E E K Q L Y N K Y P D A V
pROP 19-40   V K V A E G S S E E K A H Y S K H S D D A V
pMOP 19-39   V K V T D S G S S E E K - L Y S L H P D P I
pPOP 19-40   V K Q T N S G S S G G K A A F Q Q I H R C C

HUP  23-44   A T W L N P D P S Q K Q N L L A P Q N A V S
pHOP 41-62   A T W L N P D P S Q K Q N L L A P Q N A V S
pROP 41-62   A T W L K P D P S Q K Q N L L A P Q N S V S
pMOP 40-61   A T W L V P D P S Q K Q N L L A P Q N A V S
pPOP 41-62   S H I V K P D P S Q K Q T E L A P Q N T I S
```

BIOLOGICAL REGULATION OF MINERALIZATION

REFERENCE TO GOVERNMENT GRANT

This work was supported in part by research grants from the National Institutes of Health, grant numbers DK-33501, DK-07006, DK-30280, and AR-20553. The United States Government may have certain rights in this invention.

BACKGROUND OF THE INVENTION

Urinary tract stone disease is a common human malady. The vast majority of stones formed in the urinary space are mineralized with calcium salts. Meyer et al., *Invest. Urol.*, Vol. 13, pp. 36-39 (1975); Coe et al., *Kidney Int.*, Vol. 38, pp. 625-631 (1990). Although normal urine is frequently supersaturated with respect to calcium oxalate, inhibitors are thought to protect most humans from the formation of stones. Nakagawa et al., *J. Biol. Chem.*, Vol. 258, pp. 12594-12600 (1983). The most abundant protein in normal urine, Tamm-Horsfall protein (TH), Tamm et al., *Proc. Soc. Exp. Biol. Med.*, Vol. 74, pp. 108-114 (1950), however, has been found to be inactive as an inhibitor of crystal growth, Worcester et al., *Am. J. Physiol.*, 255, F1197-F1205 (1988), and attempts to identify proteins or other factors that fill this role have heretofore been only partially successful.

The discovery of factors present in urine responsible for preventing the formation of kidney stones would have potential therapeutic and diagnostic benefit to those suffering from such afflictions. The present invention is directed to addressing these, as well as other, important needs.

SUMMARY OF THE INVENTION

The present invention is directed to the discovery that aspartic acid-rich proteins comprising the sequence (starting at the N-terminus)

Val—Lys—Gln—Ala—Asp—Ser—Gly—Ser—Ser—Glu—
Glu—Lys—Gln—Leu—Tyr—Asn—Lys—Tyr—Pro—Asp—
Ala—Val—Ala—Thr—Trp—Leu—Asn—Pro—Asp—Pro—
Ser—Gln—Lys—Gln—Asn—Leu—Leu—Ala—Pro—Gln—
Asn—Ala—Val—Ser—Ser—Glu—Glu—Thr—Asn—Asp—
Phe—Lys—Gln—Thr—Leu—Pro—Ser—Lys—Ser—
Asn—Glu—Ser—His—Asp—His—Met—Asp—Asp—Met—
Asp—Asp—Glu—Asp—Asp—Asp—Asp—His—Val—Asp—
Ser—Gln—Asp—Ser—Ile—Asp—Ser—Asn—Asp—Ser—
Asp—Asp—Val—Asp—Asp—Thr—Asp—Asp—Ser—His—
Gln—Ser—Asp—Glu—Ser—His—His—Ser—Asp—Glu—
Ser—Asp—Glu—Leu—Val—Thr—Asp—Phe—Pro—Thr—
Asp—Leu—Pro—Ala—Thr—Glu—Val—Phe—Thr—Pro—
Val—Val—Pro—Thr—Val—Asp—Thr—Tyr—Asp—Gly—
Arg—Gly—Asp—Ser—Val—Val—Tyr—Gly—Ley—Arg—
Ser—Lys—Ser—Lys—Lys—Phe—Arg—Arg—Pro—Asp—
Ile—Gln—Tyr—Pro—Asp—Ala—Thr—Asp—Glu—Asp—
Ile—Thr—Ser—His—Met—Glu—Ser—Glu—Glu—Leu—
Asn—Gly—Ala—Tyr—Lys—Ala—Ile—Pro—Val—Ala—
Gln—Asp—Leu—Asn—Ala—Pro—Ser—Asp—Trp—Asp—
Ser—Arg—Gly—Lys—Asp—Ser—Tyr—Glu—Thr—Ser—
Gln—Leu—Asp—Asp—Gln—Ser—Ala—Glu—Thr—His—
Ser—His—Lys—Gln—Ser—Arg—Leu—Tyr—Lys—Arg—
Lys—Ala—Asn—Asp—Glu—Ser—Asn—Glu—His—Ser—
Asp—Val—Ile—Asp—Ser—Gln—Glu—Leu—Ser—Lys—
Val—Ser—Arg—Glu—Phe—His—Ser—His—Glu—Phe—
His—Ser—His—Glu—Asp—Met—Leu—Val—Val—Asp—
Pro—Lys—Ser—Lys—Glu—Glu—Asp—Lys—His—Leu—
Lys—Phe—Arg—Ile—Ser—His—Glu—Leu—Asp—Ser—
Ala—Ser—Ser—Glu—Val—Asn a sequence which is referred to herein as SEQ ID NO 1, as well as proteins having substantial homology thereto, and active peptide portions of the foregoing, are active modulators of mineralization events in mammals, serving as effective inhibitors of calcium oxalate crystal growth. These proteins, which can be isolated from urine, and peptide portions thereof, are useful as therapeutic agents, such as in the treatment of kidney stone disease.

The present invention is also directed to the discovery of extremely active and novel peptide portions contained in the foregoing protein SEQ ID NO 1. One highly active portion is a peptide comprising the sequence His—Asp—His—Met—Asp—Asp—Met—Asp—Asp—Glu—
Asp—Asp—Asp—Asp—His—Val—Asp—Ser—Gln—Asp—
Ser—Ile—Asp—Ser—Asn—Asp such peptide being referred to herein as SEQ ID NO 2. Another highly active portion is a peptide comprising the sequence Asn-Asp-Ser-Asp-Asp-Val-Asp-Asp-Thr-Asp-Asp-Ser-His-Gln such peptide being referred to herein as SEQ ID NO 3. A further highly active portion is a peptide comprising the sequence His—Asp—His—Met—Asp—Asp—Met—Asp—Asp—Glu—
Asp—Asp—Asp—Asp—His—Val—Asp—Ser—Gln—Asp—
Ser—Ile—Asp—Ser—Asn—Asp—Ser—Asp—Asp—Val—
Asp—Asp—Thr—Asp—Asp—Ser—His—Gln such peptide being referred to herein as SEQ ID NO 4, that peptide representing a combination of peptides SEQ ID NO 2 and SEQ ID NO 3. All three of the foregoing peptides, that is, SEQ ID NOs 2-4, as well as peptides having substantial homology thereto, have excellent utility as therapeutic agents, including usefulness in the treatment of kidney stone disease.

Accordingly, the present invention is further directed to pharmaceutical compositions for treating kidney stone disease comprising an effective amount of the subject proteins or peptides and a pharmaceutically acceptable carrier and/or diluent. The invention is also directed to methods for treating kidney stone disease in a patient comprising administering to the patient an effective amount of the subject protein or peptides.

The present invention is also directed to hybridomas capable of producing monoclonal antibodies to the foregoing proteins and peptides, and to the monoclonal antibodies so produced.

The monoclonal antibodies produced by the hybridomas of the present invention are capable of specifically binding to at least one antigenic determinant of the proteins and peptides. Thus, such monoclonal antibodies find uses, for example, in immunopurification processes for the extraction of the proteins and peptides, and the present invention is further directed to the same. The immunopurification process can be carried out by passing a sample containing proteins or peptides of the invention through an immunoabsorbent column which comprises a monoclonal antibody of the invention bound to a solid phase support.

Such monoclonal antibodies are also useful as diagnostic agents for certain diseases or conditions characterized by an excess or deficiency of proteins or peptides of the invention. Thus, the present invention encompasses immunoassays for detecting the presence of the subject proteins or peptides, such immunoassays comprising contacting fluid of the patient with a monoclonal antibody of the invention and screening for protein-antibody or peptide-antibody interactions (hereinafter referred to collectively as protein-antibody interactions). In addition, the invention contemplates diagnostic kits comprising a protein or peptide of the invention, and a monoclonal antibody to that protein or peptide, in combination with conventional diagnostic kit components. Examples of diseases or conditions for which such immunoassays and/or diagnostic kits are applicable, include kidney stone disease (where a deficiency of the proteins or peptides in a patient's urine and/or blood indicates potential kidney stone disease), certain lymphoid tumors or bone tumors (where an excess of the proteins or peptides in a patient's urine and/or blood indicates the potential magnitude of certain lymphoid or bone tumors), osteoporosis (where an excess of the proteins or peptides in a patient's urine and/or blood indicates potential osteoporosis), susceptability to infections by obligatory intracellular organisms such as Ricketsia, Mycobacteria, and Plasmodia (where a deficiency of the proteins or peptides in urine and/or blood indicates potential susceptability to such infections), and autoimmune diseases (where a deficiency of the proteins or peptides in urine and/or blood indicates potential autoimmune disease).

In addition, polyclonal antibodies are also useful as diagnostic agents for certain diseases or conditions, and in immunopurification processes, and as such are within the scope of the invention.

Finally, the present invention includes the use of the monoclonal antibodies as therapeutic agents, such as in the treatment of osteoporosis. Thus, the present invention is further directed to methods for treating osteoporosis in a patient comprising administering to the patient an effective amount of the subject monoclonal antibodies.

These and other aspects of the invention will become more apparent from the following detailed description when taken in conjunction with the following figures.

BRIEF DESCRIPTION OF THE FIGURES

FIG. 3 shows a comparison of the aligned N-terminal amino acid sequences of a protein of the present invention (Human Uropontin; HUP) isolated by immunoaffinity chromatography, with human osteopontin (pHOP), rat osteopontin (pROP), mouse osteopontins (from skin, macrophages and thymocytes) (pMOP), and porcine osteopontin (pPOP) as derived from cDNA sequences. Conserved amino acids in this sequence are indicated by the enclosure. The abbreviations for the amino acids employed shown in the figure are the standard one-letter abbreviations.

DETAILED DESCRIPTION OF THE INVENTION

Figure 1A:
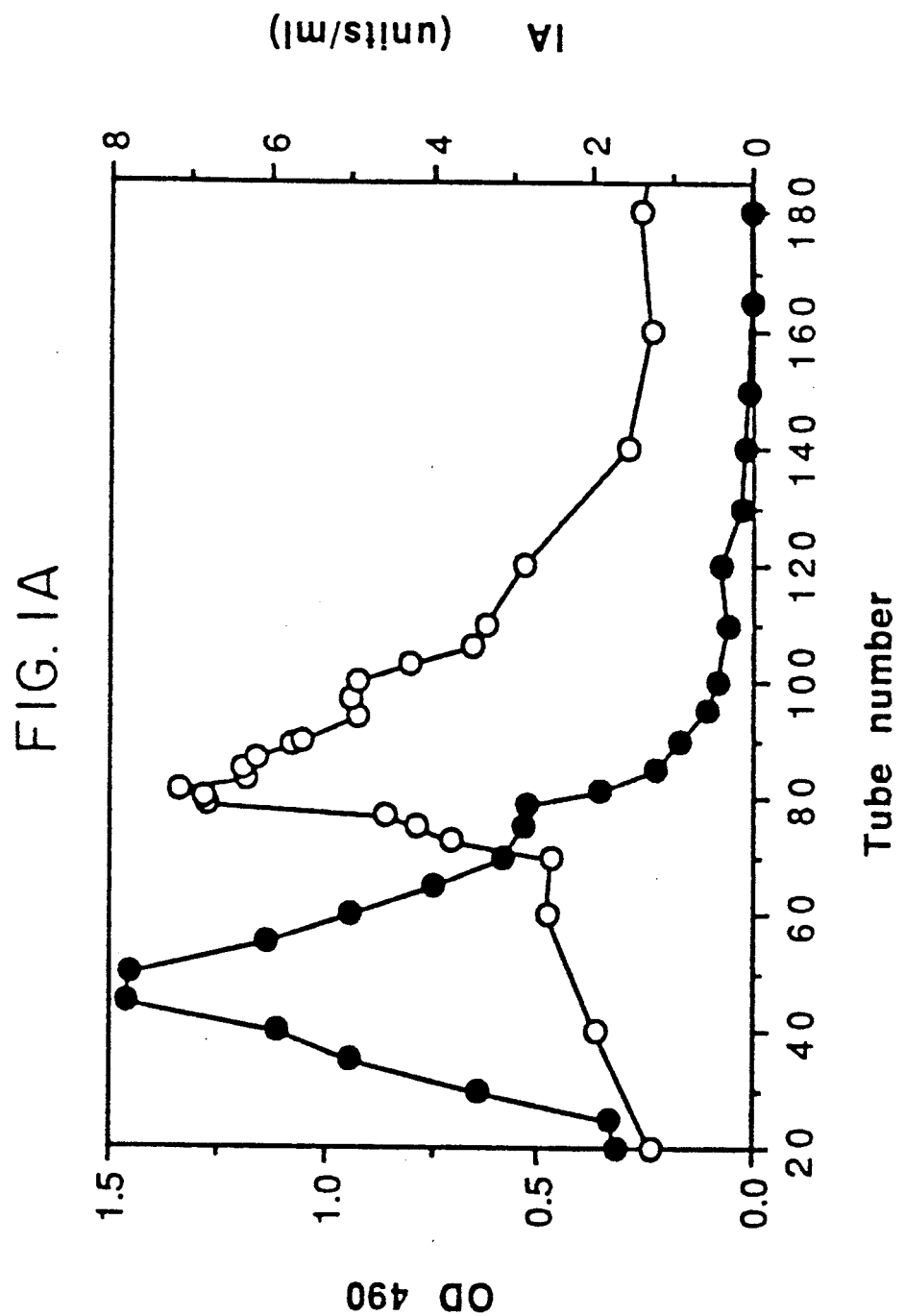
FIG. 1A shows a DEAE-cellulose chromatogram of gradient salt elution (0.1M to 0.4M NaCl) of the DEAE batch eluate obtained from normal human urine partially depleted of TH by salt precipitation. The greatest reactivity of tubes by ELISA (closed circles) using antisera prepared by immunization with the protein fraction corresponding to the main inhibitory peak (identified by functional assay of $C^{14}$ oxalate incorporation into seed crystals) is present in tubes that eluted earlier than the main inhibitory peak (open circles).

The proteins of the present invention include the protein of SEQ ID NO 1 (set forth above). The protein of the SEQ ID NO 1, which was isolated from human urine by immunoaffinity chromatography, has been found by micro-sequencing and amino acid analysis to be homologous to human osteopontin, a protein which is encoded, by the human osteopontin (OPN) gene. Human osteopontin (and the gene encoding that protein) is shown and described in Kiefer et al., *Nucleic Acids Res.*, Vol. 17, pp. 3306-3306 (1989) and Young et al, *Genomics*, Vol. 7, pp. 491-502 (1990), the disclosures of each of which are incorporated herein by reference in their entirety. At times herein, the protein of SEQ ID NO 1 will be referred to as human uropontin or HUP, a name which reflects the fact that it has been isolated from urine.

The present invention is also directed to peptides having substantial homology to the human uropontin protein of SEQ ID NO 1. By the phrase proteins having substantial homology, it is meant natural genetic variants of the peptides of SEQ ID NO 1. As those skilled in the art will recognize, a number of other naturally occuring pontin proteins have been identified, such as, for example, an isoform of the human osteopontin of SEQ ID NO 1, rat osteopontin, mouse osteopontins (from skin, macrophages and thymocytes), and porcine osteopontin, and these and other natural variants are examples of substantially homologous proteins, as that phrase is employed herein. An isoform of human osteopontin (and the gene encoding that protein) is shown and described, for example, in Young et al., *Genomics*, Vol. 7, pp. 491-502 (1990), and has the following sequence

```
Val—Lys—Gln—Ala—Asp—Ser—Gly—Ser—Ser—Glu—
Glu—Lys—Gln—Leu—Tyr—Asn—Lys—Tyr—Pro—Asp—
Ala—Val—Ala—Thr—Trp—Leu—Asn—Pro—Asp—Pro—
Ser—Gln—Lys—Gln—Asn—Leu—Leu—Ala—Pro—Gln—
Thr—Leu—Pro—Ser—Lys—Ser—Asn—Glu—Ser—His—
Asp—His—Met—Asp—Asp—Met—Asp—Asp—Glu—Asp—
Asp—Asp—Asp—His—Val—Asp—Ser—Gln—Asp—Ser—
Ile—Asp—Ser—Asn—Asp—Ser—Asp—Asp—Val—Asp—
Asp—Thr—Asp—Asp—Ser—His—Gln—Ser—Asp—Glu—
Ser—His—His—Ser—Asp—Glu—Ser—Asp—Glu—Leu—
Val—Thr—Asp—Phe—Pro—Thr—Asp—Leu—Pro—Ala—
Thr—Glu—Val—Phe—Thr—Pro—Val—Val—Pro—Thr—
Val—Asp—Thr—Tyr—Asp—Gly—Arg—Gly—Asp—Ser—
Val—Val—Tyr—Gly—Leu—Arg—Ser—Lys—Ser—Lys—
Lys—Phe—Arg—Arg—Pro—Asp—Ile—Gln—Tyr—Pro—
Asp—Ala—Thr—Asp—Glu—Asp—Ile—Thr—Ser—His—
Met—Glu—Ser—Glu—Glu—Leu—Asn—Gly—Ala—Tyr—
Lys—Ala—Ile—Pro—Val—Ala—Gln—Asp—Leu—Asn—
Ala—Pro—Ser—Asp—Trp—Asp—Ser—Arg—Gly—Lys—
Asp—Ser—Tyr—Glu—Thr—Ser—Gln—Leu—Asp—Asp—
Gln—Ser—Ala—Glu—Thr—His—Ser—His—Lys—Gln—
Ser—Arg—Leu—Tyr—Lys—Arg—Lys—Ala—Asn—Asp—
Glu—Ser—Asn—Glu—His—Ser—Asp—Val—Ile—Asp—
Ser—Gln—Glu—Leu—Ser—Lys—Val—Ser—Arg—Glu—
Phe—His—Ser—His—Glu—Phe—His—Ser—His—Glu—
Asp—Met—Leu—Val—Val—Asp—Pro—Lys—Ser—Lys—
Glu—Glu—Asp—Lys—His—Leu—Lys—Phe—Arg—Ile—
Ser—His—Glu—Leu—Asp—Ser—Ala—Ser—Ser—Glu—
Val—Asn
``` such protein being referred to herein as SEQ ID NO 5. Rat osteopontin (and the gene encoding that protein) is shown and described, for example, in Oldberg et al., *Proc. Natl. Acad. Sci. USA*, Vol. 83, pp. 8819-8823 (1986), and is referred to therein as rat osteopontin. Porcine osteopontin (and the gene encoding that protein) is shown and described, for example, in Wrana et al., *Nucleic Acids Res.*, Vol. 17, pp. 10119-10119 (1989), and is referred to therein as porcin osteopontin. Mouse osteopontins (and genes encoding those proteins) are shown and described, for example, in Craig et al., *J. Biol. Chem.*, Vol. 264, pp. 9682-9689 (1989), Miyazaki et al., *Nucleic Acids Res.*, Vol. 17, pp. 3298-3298 (1989), and Patarca et al., *J. Exp. Med.*, Vol. 170, pp. 145-161 (1989), and are referred to therein as 2ar osteopontin, osteopontin and eta-1, respectively. The disclosures of each of the forgoing references are incorporated herein by reference in their entirety. These and other substantially homologous proteins will be readily apparent to those skilled in the art once armed with the present disclosure.

The present invention also includes active portions of the protein of SEQ ID NO 1 and the proteins substantially homologous thereto. By active portions it is meant portions which are at least substantially as active as the protein of SEQ ID NO 1 or the proteins substantially homologous thereto, with regard to any one of the various activities and utilities set forth herein for such proteins. The identification of active proteins will be within the ambit of the skilled artisan once provided with the present disclosure.

Three extremely active and novel portions of the protein SEQ ID NO 1 are those peptides identified as SEQ ID NO 2, SEQ ID NO 3, and SEQ ID NO 4. The foregoing peptides, as well as peptides having substantial homology thereto, have excellent utility as therapeutic agents for the treatment of kidney stone disease.

For example, peptides SEQ ID NO 2 and SEQ ID NO 3 (MW 3200 and 1700, respectively) are highly active inhibitors of calcium oxalate crystal growth at 1-10 $\mu$g/ml, with specific activities comparable on a weight basis to the native protein of SEQ ID NO 1. The novel peptides SEQ ID NO 2-4 may be used alone, or included as part of a larger peptide. To provide the best balance of activity versus toxicity, preferably any larger peptide which includes peptide SEQ ID NOs 2-4 is of a length of no greater than about 200 amino acids (inclusive of the fragments SEQ ID NOs 2-4), more preferably no greater than about 150 amino acids, even more preferably no greater than about 100 amino acids, and still more preferably no greater than about 50 amino acids.

The foregoing proteins and peptides may be obtained in various fashions, as will be apparent to those skilled in the art once armed with the present disclosure. For example, the proteins and/or peptides may be isolated from body fluids such as urine or blood using the techniques disclosed herein, may be obtained using standard recombinant DNA techniques such as those described in Sambrook, Fritsch, & Maniatus, *Molecular Cloning: A Laboratory Manual*, Vols. 1-3, 2nd ed. (Cold Springs Harbor Laboratory Press, N.Y. 1989), based on the published gene sequences of the osteopontin proteins, and/or by using conventional peptide synthesis methodology such as is described in Houghton, *Proc. Natl. Acad. Sci. USA*, Vol. 82, pp. 5131-5135 (1985). The disclosures of both of the foregoing publications are incorporated herein by reference in their entirety.

The proteins and peptides of the present invention are useful as therapeutic agents such as in the treatment of kidney stone disease. Accordingly, the present invention contemplates pharmaceutical compositions for treating kidney stone disease comprising an effective amount of the subject proteins or peptides and a pharmaceutically acceptable carrier and/or diluent. The present invention also contemplates methods for treating kidney stone disease in a patient comprising administering to the patient an effective amount of the subject proteins or peptides.

Acceptable carriers and diluents which can be employed in connection with the subject proteins or peptides in the subject pharmaceutical compositions are well known in the pharmaceutical art, and are described, for example, in Remington's *Pharmaceutical Sciences*, Gennaro, A. R., ed., Mack Publishing Co., Easton, Pa. (1985). In practicing the methods of the invention, the proteins and/or peptides can be employed alone in the form of a composition, or in combination with other pharmaceutical agents. Administration may be carried out using a variety of dosage forms, preferably, however, administration is by intravenous injection or by direct injection into the urinary system. The useful dosage to be administered and the mode of administration will vary depending upon the age, weight, and particular patient treated. By way of general guidance, a dosage sufficient to achieve a level of protein or peptide between about 1 and about 100 $\mu$g/ml in the blood stream or the urinary system may be administered. Typically, therapy is initiated at lower dosage levels with dosage being increased until the desired effect is achieved. The patient treated may be any type of mammal, but preferably is a human.

Hybridomas capable of producing monoclonal antibodies to the foregoing proteins and peptides, and the monoclonal antibodies so produced, are also within the ambit of the present invention. The hybridomas and monoclonal antibodies of the invention may be obtained by the techniques described herein. In general, the subject hybridomas and monoclonal antibodies may be prepared by hyperimmunizing a series of rats (such as Lewis rats) with the proteins or peptides of the invention, obtaining spleen cells ($\beta$-lymphocytes) from these rats, and then fusing these spleen cells to myeloma cells (such as Sp2/0-Ag14 myeloma cells) with polyethylene glycol or the like. The resultant hybridoma cells can then be cloned, and antibody-secreting hybridomas can be selected for their ability to react with the proteins or peptides used for immunization. Further details on the procedures for producing hybridomas and monoclonal antibodies is set forth in the examples provided below. In addition, the preparation of hybridomas and monoclonal antibodies is described, for example, in Harlow & Lane, *Antibodies: A Laboratory Manual* (Cold Springs Harbor Laboratory Press, N.Y. 1989), the disclosures of which are incorporated herein by reference in their entirety.

Polyclonal antibodies to the subject proteins and peptides are also within the ambit of the invention. Such polyclonal antibodies may be produced using standard techniques, for example, by immunizing a rabbit (such as a New Zealand rabbit) or a rat with a protein or peptide of the invention, removing serum from the rabbit, and then harvesting the resultant polyclonal antibodies from the serum. If desired, the polyclonal antibodies may be used as an IgG fraction or may be further purified in varying degrees. Procedures for preparing, harvesting and purifying polyclonal antibodies are well known in the art, and are described, for example, in Garvey et al., *Methods In Immunology: A Laboratory Text for Instruction and Research*, 3rd ed., Chs. 22, 24-30, W. A. Benjamin Inc. (Reading Mass. 1977), the disclosures of which are incorporated herein by reference in their entirety.

The monoclonal antibodies produced by the hybridomas of the present invention and the polyclonal antibodies of the subject invention are capable of specifically binding to at least one antigenic determinant of the proteins and peptides of the invention. Thus, such monoclonal and/or polyclonal antibodies may be employed, for example, in immunopurification processes for the extraction of the subject proteins and peptides, and the present invention is further directed to the same. The immunopurification process can be carried out by passing a sample containing proteins or peptides of the invention through an immunoabsorbent column which comprises a monoclonal and/or polyclonal antibody of the invention bound to a solid phase support. As will be apparent to those skilled in the art, various materials can be employed as the solid phase support. Such materials include polystyrene, Affigel-10 ™, agarose beads, and cyanogen bromide activated Sepharose 4B ™. Immunoabsorbent columns are well known in the art and are described, for example, in *Affinity Chromatography: A Practical Approach*, P. D. Dean, W. S. Johnson, and F. A. Middle, eds. (IRL press, Washington, D.C., 1985). Biological samples which may contain extractable proteins and peptides include blood, urine, and/or breast milk.

Such monoclonal antibodies and/or polyclonal antibodies are also useful as diagnostic agents for the detection of certain diseases or conditions characterized by an excess or deficiency of the proteins or peptides of the invention. Thus, the present invention encompasses immunoassays for determining the levels of the subject proteins or peptides, such immunoassays comprising contacting fluid of the patient with a monoclonal and/or polyclonal antibody of the invention and screening for protein-antibody interactions. Applications of such diagnostic methods include, for example, the evaluation of patients suspected of having kidney stone disease, a disease where a deficiency in the normal amount of the proteins or peptides in a patient's urine and/or blood indicates the possible existence of such a malady. With respect to the diagnostic utilities decribed herein, the phrase a normal amount of proteins or peptides should be taken to mean that amount of proteins or peptides which would statistically be present in the fluids of normal patient of the same weight and age. Since activated lymphoid tumors and bone tumors secrete an excess amount of the proteins or peptides of the present invention, as compared to normal, the monoclonal and/or polyclonal antibodies of the invention can be used to diagnose the potential magnitude of lymphoid or bone tumors in a patient supected or known to have such tumors by an immunoassay of the urine and/or blood of the patient. Senger et al., *Cancer Research*, Vol. 48, pp. 5770-5774 (1988); Senger et al., *Biochem. Biophys. Acta*, Vol. 996, pp. 43-48 (1989); and Craig et al., *J. Biol. Chem.*, Vol. 264, pp. 9682-9689 (1989). Diagnostic applications with respect to osteoporosis are also within the ambit of the present invention, wherein the presence of a greater than normal amount of proteins or peptides in the urine and/or blood of a patient suspected of suffering from osteoporosis provides an indication of the potential existence of this disease. Further, a deficiency of the proteins or peptides in the urine and/or blood can be an indicator of a susceptability to infections by obligatory intracellular organisms such those bacteria of the genus Ricketsia, Mycobacteria, and Plasmodia. Singh et al., *J. Exp. Med.*, Vol. 171,pp.1931-1942 (1990); Patarca et al., *J. Exp. Med.*, Vol. 170, pp. 145-161 (1989). As those skilled in the art would recognize, obligatory intracellular organisms are those bacterial organisms which must enter the cell in order to survive and/or propogate. Exemplary infections involving bacteria of the genus Ricketsia include scrub typhus infection in mice. Exemplary infections involving bacteria of the genus Mycobacteria include tuberculosis. Exemplary infections involving bacteria of the genus Plasmodia include malaria. Moreover, a deficiency of the proteins or peptides in the urine and/or blood can be a indicator of autoimmune disease, such as systemic lupus, erythematosis, mixed connective tissue disease, thyroiditus, and rheumatoid arthritus. Singh et al., *J. Exp. Med.*, Vol. 171,pp. 1931-1942 (1990); Patarca et al., *J. Exp. Med.*, Vol. 170, pp. 145-161 (1989). Employed as described above, the present monoclonal and/or polyclonal antibodies provide a new and important tool for clinical diagnosis and prognosis efforts in the foregoing areas.

The present invention may also be employed diagnostically in immunoassays for determining the relative amounts of proteins or peptides of the invention present in a patient. Such assays may be carried out by contacting blood and/or urine from a patient with a monoclonal and/or polyclonal antibody to one protein or peptide of the invention, such as protein SEQ ID NO 1, and screening for protein-antibody interactions, while concurrently, subsequently, or prior to contacting blood and/or urine from the same patient with a monoclonal and/or polyclonal antibody to another protein or peptide of the invention, such as SEQ ID NO 2, and also screening for protein-antibody interactions. The amount of protein-antibody interactions in the two screenings can then be compared to ascertain the relative amounts of the two proteins or peptides in the patient. This can then be compared against the relative amounts possessed by a normal patient to ascertain whether the patient has an improper balance of proteins or peptides.

The present invention may also be employed diagnostically in immunoassays for monitoring the levels of the proteins or peptides of the invention present in a patient during protein or peptide therapy. Such assays may be carried out by contacting blood and/or urine from a patient with a monoclonal and/or polyclonal antibody to a protein or peptide of the invention, and screening for protein-antibody interactions.

As will be apparent to one skilled in the art, the amount of monoclonal and/or polyclonal antibody employed in the diagnostic methods may vary. By way of general guidance, the monoclonal and/or polyclonal antibody should be present in an amount sufficient to permit significant binding to the proteins or peptides. As those skilled in the art will recognize, an amount between about 1 to about 5 µg monoclonal and/or polyclonal antibodies per ml of blood or urine fluids is generally suitable, although larger or smaller amounts of monoclonal and/or polyclonal antibodies may also be used. Screening can be carried out using conventional methods readily apparent to those skilled in the art, such as enzyme immunoassay or radioimmunoassay.

The invention also contemplates diagnostic kits comprising a protein or peptide of the invention and a monoclonal and/or polyclonal antibody to that protein or peptide, in combination with conventional diagnostic kit components. Using the kit components, a sample of a patient's blood or urine could be tested in, for example, an ELISA assay, using the monoclonal and/or polyclonal antibodies in the kit, and can be compared with the results of a similar test which employs both the protein or peptide and the monoclonal antibody in the kit as a standard. Conventional diagnostic kit components will be readily apparent to those skilled in the art, and are disclosed in numerous publications, including *Antibodies: A Laboratory Manual* (Cold Spring Harbor Laboratory Press, N.Y. 1989), the disclosures of which are incorporated herein by reference in their entirety. Conventional diagnostic kit components may include such items as, for example, microtiter plates, buffers (such as, for example, EDTA buffer, Tris buffer, etc.), secondary buffers (such as, for example, peroxidase conjugated anti-rat IgG or anti-rabbit IgG), and other standard reagents and components.

Further, the present invention encompasses the use of the monoclonal antibodies as therapeutic agents, such as in the treatment of osteoporosis. Thus, the present invention contemplates pharmaceutical compositions for treating osteoporosis comprising an effective amount of the subject monoclonal antibodies and a pharmaceutically acceptable carrier and/or diluent. The present invention also contemplates methods for treating osteoporosis, a disease characterized by features suggestive of too much of the subject proteins or peptides as compared to normal, in a patient comprising administering to the patient an effective amount of the subject monoclonal antibodies. The use of the monoclonal antibodies as immunoprophylactic reagents in the treatment of osteoporosis represents a significant new approach in dealing with this disease.

Acceptable carriers and diluents which can be employed in connection with the monoclonal antibodies in the subject pharmaceutical compositions are well known in the pharmaceutical art, and are described, for example, in Remington's *Pharmaceutical Sciences*, Gennaro, A. R., ed., Mack Publishing Co., Easton, Pa. (1985). In practicing the methods of the invention, the monoclonal antibodies can be employed alone in the form of a composition, or in combination with other pharmaceutical agents. Administration may be carried out using a variety of dosage forms, preferably, however, administration is by intravenous injection. The useful dosage to be administered and the mode of administration will vary depending upon the age, weight, and particular patient treated. By way of general guidance, a dosage sufficient to achieve a level of protein or peptide between about 0.1 and about 10 µg/ml in the blood stream or the urinary system may be administered. Typically, therapy is initiated at lower dosage levels with dosage being increased until the desired effect is achieved. The patient treated may be any type of mammal, but preferably is a human.

The present invention is further described in the following examples. These examples are not to be construed as limiting the scope of the appended claims.

EXAMPLES

Example 1

Human urine samples were maintained throughout the procedures in the presence of 0.02% sodium azide, and 2 protease inhibitors, 0.5 mM phenylmethanesulfonyl fluoride and 1.0 mM N-ethylmaleimide. The urine sample was first partially depleted of Tamm-Horsfall protein (TH) by salt precipitation followed by centrifugation at 5,000×g for 30 minutes, as described in Tamm et al., *Proc. Soc. Exp. Biol. Med.*, Vol. 74, pp. 108–114 (1950). TH-depleted urine was then adsorbed to DEAE-cellulose, batch eluted and fractionated by DEAE-cellulose column chromatography using a 0.1M to 0.4M NaCl linear gradient in Tris buffer, as decribed in Nakagawa et al., *J. Biol. Chem.*, Vol. 258, pp. 12594–12600 (1983).

Crystal growth inhibition of the protein fractions was assayed by measuring the inhibition of incorporation of [$^{14}$C]oxalate (available from Amersham, Arlington Heights, Ill.) into calcium oxalate monohydrate seed crystals (EM Sciences, Gibbstown, N.J.) during an incubation period of 180 minutes, using the method described in Ligabue et al., *Clin. Chim. Acta*, Vol. 98, pp. 39–46 (1979). Samples and standards (200 µl) were incubated with 2.0 ml of a metastable solution (2 mM $CaCl_2$, 0.2 mM sodium oxalate (available from Sigma, St. Louis, Mo.), 5 mM sodium cacodylate (available from Sigma), 0.15M NaCl, pH 6.0) and 10 µl of [$^{14}$C]oxalate (0.1 µCi) for 30 minutes at 37° C. in a shaking bath. After equilibration, 200 µl was removed and counted in a liquid scintillation counter ($T_o$). The remainder was incubated for 180 minutes at 37° C. with 200 µl of aged calcium oxalate seed crystal solution (1.5 mg/ml) under constant shaking. One ml samples were then removed and centrifuged (8,000×g for 2 min at 4° C.), and the radioactivity of 200 µl of each supernatant was counted ($T_{180}$).

The percent residual radioactivity in 200 µl of the centrifuge supernatants was then used to calculate the inhibitory activity (IA) of samples using the following formula:

IA [Units/ml] = 5 × (% residual radioactivity of sample − % residual radioactivity of standard)/(100 − % residual radioactivity of sample).

The protein fraction with the major inhibitory peak was identifified and set aside for further use.

Example 2
Hybridoma and Monoclonal Antibody Preparation

Hybridoma cells were derived from fusions of Sp2/0-Ag myeloma cells, with spleen cells ($\beta$-lymphocytes) from inbred Lewis rats immunized with the protein fraction from Example 1 having the major inhibitory peak. Hybridomas were selected for subcloning by limiting dilution on the basis of differential reactivity by enzyme-linked immunosorbent assays (ELISA) and used to produce monoclonal antibodies to the protein fraction of Example 1 and to TH in nude mice.

ELISAs were performed as generally described in Yoshioka et al., J. Clin. Invest., Vol. 82, pp. 1614–1623 (1988) and Clayman et al., J. Exp. Med., Vol. 161, pp. 290–305 (1985), using 96 well polyvinyl chloride microtiter plates (available from Dynatech, Chantilly, Va.). The wells were coated with antigens in 0.025M EDTA buffer, at pH 9.3 (100 $\mu$l/well) for 15 hours at 4° C., and washed three times with a blocking buffer comprising 0.5% casein (available from Fisher, Pittsburgh, Pa.), 0.01M Tris, and 0.154M NaCl, at pH 7.6. Wells were incubated With rat or rabbit IgG monoclonal or polyclonal antibodies respectively in the buffer for 60 minutes at 37° C., washed, and then incubated with peroxidase conjugated anti-rat IgG or anti-rabbit IgG (available from Cappel, West Chester, Pa.), respectively, in casein buffer for 60 minutes at 37° C. and rewashed. The substrate reaction using a buffer comprising 0.137% O-phenylenediamine (available from Aldrich Chemical Co., Milwaukee, Wis.), 0.009% $H_2O_2$ in 0.2 M Tris, and 0.15 M NaCl, at pH 6.0 was performed in the dark at room temperature and the optical density at 490 nM determined in an automated ELISA reader (available from Dynatech). In initial studies of DEAE column fractions using a sandwich ELISA, polyclonal rabbit antibody-coated plates were exposed to dilutions of column fractions and then to polyclonal rat antisera.

SDS-polyacrylamide gel electrophoresis (PAGE) was performed by the slab technique, as generally described in Laemmli, Nature, Vol. 227, pp. 68–685 (1970). Specifically, SDS-PAGE was performed using samples (6 $\mu$g) and molecular weight standards (available from Bio-Rad Laboratories, Rockville Centre, N.Y.) in 2.0% SDS, 0.02M dithiothreitol (DTT) (available from Bio-Rad Laboratories), and 0.0625M Tris, at pH 6.8 which were heated for 2 minutes at 90° C. Samples were applied to 16% polyacrylamide (available from FMC Bioproducts, Rockland, Ma.) or 5 to 18% gradient polyacrylamide slab gels containing 0.375M Tris, and 0.1% SDS, at pH 8.8. Electrophoresis was performed using a 0.025M Tris, 0.192M glycine, 0.1% SDS, pH 8.3 running buffer. Gels were then stained with silver (available from Bio-Rad Laboratories) or transferred for Western blotting.

For Western blotting, the gels were transfered to 0.2 $\mu$m nitrocellulose membranes (available from Bio-Rad Laboratories). A 100 mA constant current was applied for 16 hours in accordance with the procedure of Towbin et al., Proc. Natl. Acad. Sci. USA, Vol 76, pp. 4350–4354 (1979), after being pre-equilibrated with transfer buffer (0.025M Tris, 0.192M glycine, 20% v/v methanol). After incubation with a blocking milk buffer (5% w/v nonfat dry milk in phosphate buffered saline with 0.0001% Merthiolate, pH 7.3) for 2 hours at 37° C. to reduce background staining, membranes were incubated with the first antibody in milk buffer for 60 minutes at 37° C., washed and incubated with a peroxidase conjugated second antibody in milk buffer for 30 min at 37° C. and rewashed. The substrate reaction (0.012% $H_2O_2$, 0.024% diaminobenzidine (available from Sigma), in 0.05M Tris buffer, pH 7.4) was performed at room temperature.

Initial clones derived from the fusion of cells from rats immunized with the protein of Example 1 were selected on the basis of reactivity with the inhibitory peak by ELISA. The IgG fractions of these monoclonal antibodies in ascites harvested from nude mice were coupled to Sepharose. Absorption of aliquots of the inhibitory peak with these monoclonal antibody beads abolished reactivity to these antibodies by ELISA, but did not substantially reduce inhibitory activity. The acid eluates from these antibody-beads reacted strongly with these antibodies by ELISA but showed no inhibitory activity in functional assays. Examination of the gradient DEAE column fractions by ELISA showed that these antibodies identified ELISA peak reactivity (ELISA peak, EP) in tubes earlier than the inhibitory peak (FIG. 1A).

The eluates from these antibody beads migrated in the same position as Tamm-Horsfall protein (TH) on 16% PAGE gels and were detected in Western blots at the same position ($\sim$98 kD) by these monoclonal antibodies and by polyclonal antibodies to TH. The presence of TH in inhibitory fractions from DEAE columns was confirmed by Western blotting of PAGE gels. An ELISA analysis of DEAE column chromatography fractions using polyclonal anti-TH showed peak reactivity in a position identical to that shown in FIG. 1A. Each of the three monoclonal antibodies reacted strongly with purified human TH by ELISA.

These results were used to design a second series of subclonings using negative selection for TH. This series of subclonings lead to isolation of a functionally active protein by immunoaffinity chromatography. In accordance with the isolation procedure, partial depletion of Tamm-Horsfall protein (TH) by the classical method of salt precipitation and centrifugation was employed as an initial step. Inhibitory fractions isolated after this step were used for subsequent immunizations. Hybridoma cells were initially selected on the basis of greater ELISA reactivity of their supernatants with the protein fraction of Example 1 than with comparable concentrations of TH or the EP shown in FIG. 1A. FIG. 1A shows a DEAE chromatogram of gradient salt eluction (0.1M to 0.4M NaCl of the DEAE batch eluate obtained from normal human urine partially depleted of TH by salt precipitation. The greatest reactivity of tubes by ELISA (closed circles) using antisera to TH is present in tubes that eluted earlier than the main inhibitory peak (open circles) identified by functional assay of $C^{14}$ oxalate incorporation into seed crystals.

Figure 1B:
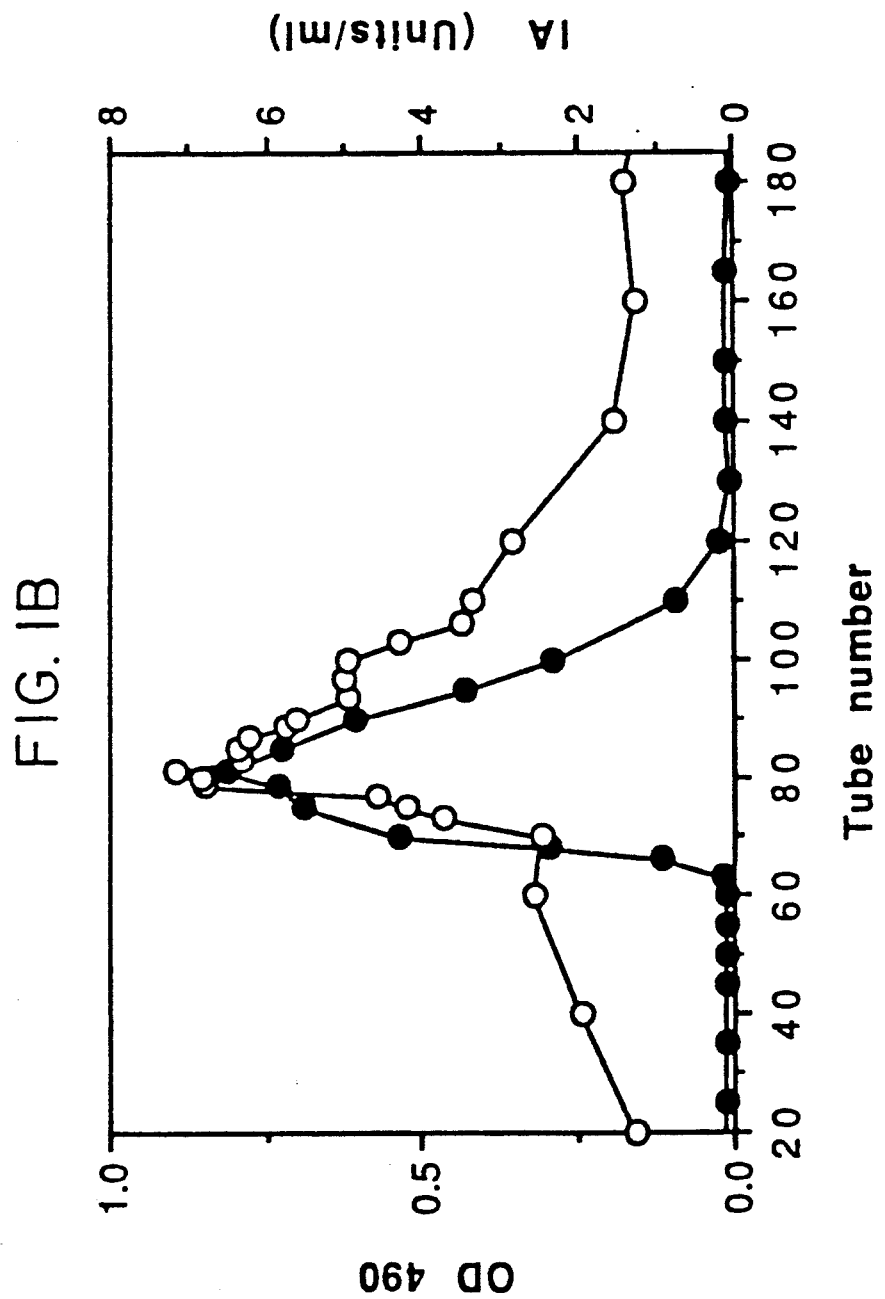
FIG. 1B shows a DEAE-cellulose chromatogram of gradient salt elution (0.1M to 0.4 M NaCl) of the DEAE-cellulose batch eluate obtained from normal human urine partially depleted of TH by salt precipitation. The greatest reactivity by ELISA detected with monoclonal antibody ZH2 (closed circles) using microtiter plates coated with column fractions coincided with the protein fraction corresponding to the main inhibitory peak (open circles) which had been identified by functional assay of $C^{14}$ oxalate incorporation into seed crystals.
Figure 1C:
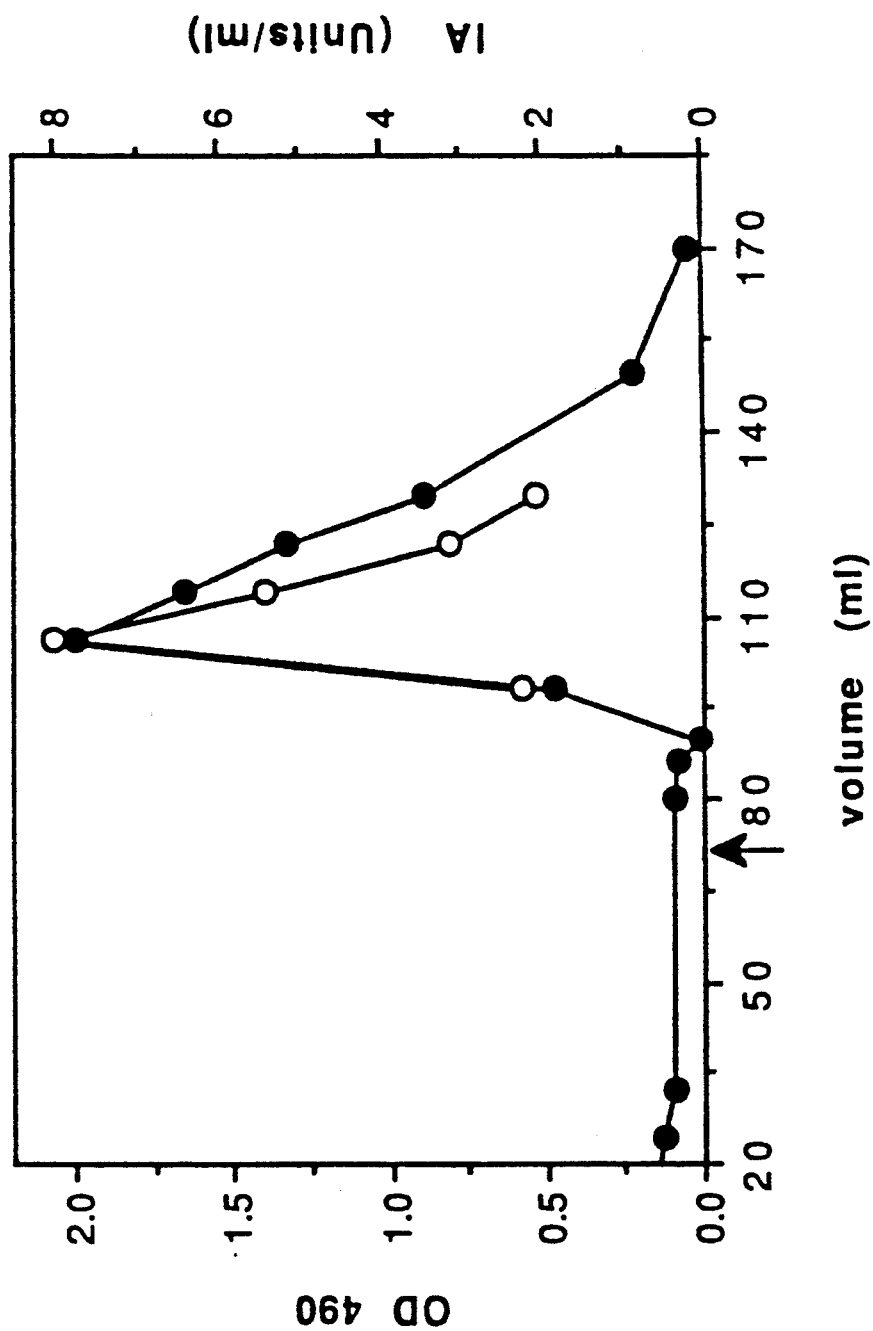
FIG. 1C shows elution of ELISA reactivity of ZH2 (closed circles) and crystal growth inhibitory activity (open circles) from an affinity column of monoclonal antibody ZH2 beads that had been exposed to an aliquot of the protein fraction from normal human urine corresponding to the main inhibitory peak (identified by inhibition of calcium oxalate crystal growth), and then extensively washed with phosphate buffered saline at pH 7.4. Elution with a 0.2M glycine pH 2.8 buffer was started at the arrow.
Figure 2:
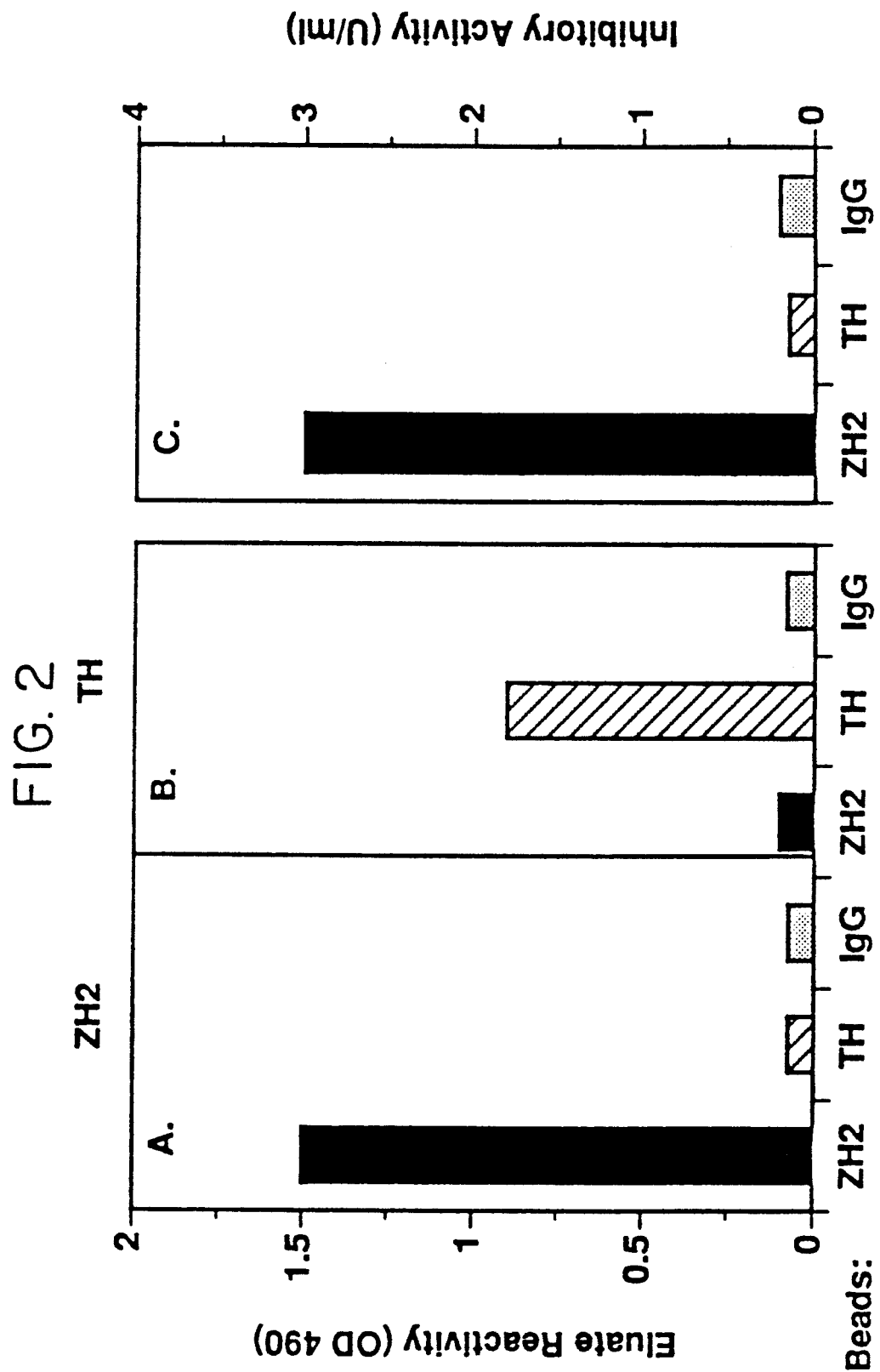
FIG. 2A shows ELISA reactivity detected by monoclonal antibody ZH2 (a monoclonal to the inhibitory protein in normal human urine) in acid eluates from monoclonal antibody ZH2 beads, anti-TH beads, and normal IgG beads after equivalent exposure to aliquots of protein fraction from human urine corresponding to the main inhibitory peak (inhibition of calcium oxalate crystal growth).
FIG. 2B shows ELISA reactivity detected by monoclonal anti-TH in the same eluates as in FIG. 2A.
FIG. 2C shows crystal growth inhibitory activity in the same eluates as in FIG. 2A.

Two of the initial supernatants of hybridomas had greater reactivity with the main inhibitory peak than with TH by ELISA, and these hybidomas were selected for subcloning. The monoclonal antibodies produced by one subclone, ZH2, were studied in greatest detail because the supernatant of this clone reacted strongly with the inhibitory protein peak, but not with TH. Analysis of the fractions obtained by DEAE-cellulose column chromatography and by acid elution from monoclonal antibody immunoaffinity columns demonstrated that the greatest immunoreactivity with antibody ZH2 was present in the same tubes as those with the greatest inhibitory activity (FIGS. 1B and 1C). Absorption of aliquots of the inhibitory protein peak (tubes 70-90 from FIG. 1B) with 200 μl of monoclonal antibody beads decreased the ELISA reactivity detected by ZH2, but not by anti-TH antibody in the supernatants of ZH2 beads. Similar absorptions using anti-TH beads, and normal rat IgG beads did not decrease reactivity detected by ZH2, but did eliminate anti-TH reactivity in the supernatant absorbed with anti-TH beads. Acid eluates from the antibody beads showed reactivity by ELISA with their respective antibodies (FIGS. 2A and 2B). Inhibitory activity was detected in the eluate from ZH2 beads (FIG. 2C).

Example 3

Immunoaffinity Purification

Solid-phase immunoabsorbents were prepared by coupling IgG fractions of monoclonal antibodies from Example 2 to cyanogen bromide-activated Sepharose 4B (5 mg protein/ml beads). After exposure to aliquots of inhibitory fractions of human urine, the monoclonal antibody beads were extensively washed with phosphate buffered saline, pH 7.4, followed by elution with a 0.2M glycine pH 2.8 buffer. Eluates were neutralized and dialysed against a 0.05M Tris, 0.05M NaCl, pH 7.3 buffer prior to characterization of inhibitory activity and immunologic reactivity. The protein isolated by immunoaffinity chromatography was further purified by reverse-phase HPLC, using the procedures described in Przysiecki et al, *Proc. Natl. Acad. Sci. USA*, Vol. 84, pp. 7858-7860 (1987), prior to analysis of amino acid composition and N-terminal sequence.

Affinity columns of ZH2 beads were used for purification of an inhibitory protein based on the results in Example 2. The elution patterns for inhibitory activity and ELISA reactivity with ZH2 of these large columns were substantially the same as those shown in FIG. 1B. Approximately 30% of the protein in 3-9 liter lots of TH-depleted urine (n=4) was isolated by 0.4M NaCl elution after batch adsorption to DEAE-cellulose. Approximately 4% of the protein in DEAE batch eluates applied to ZH2 affinity columns was recovered in acid eluates. The specific activity (Inhibitory units/mg) of ZH2 eluates was 3.3 to 11 fold greater than corresponding DEAE eluates (n=4).

Example 4

Protein Characterization

Analysis of N-terminal sequence and amino acid composition of the purified protein of Example 3 was carried out by using a standard automated sequence analyzer, as described in Przysiecki et al., *Proc. Natl. Acad. Sci USA*, Vol. 84, pp. 7858-7860 (1987). The results are shown in FIG. 3 (denoted as HUP), and Table 1 (denoted as human uropontin), respectively.

A comparison of the N-terminal sequence determined for uropontin with protein sequences from the literature and from the Swissprot database, commercially available from the University of Geneva, shown in FIG. 3, revealed identity with human osteopontin (HOP) (shown in Kiefer et al., *Nucleic Acids Res.*, Vol. 17, pp. 3306-3306 (1989)), rat osteopontin (ROP) (shown in Oldberg et al., *Proc. Natl. Acad. Sci. USA*, Vol. 83, pp. 8819-8823 (1986)), porcine osteopontin (POP) (shown in Wrana et al., *Nucleic Acids Res.*, Vol. 17, pp. 10119-10119 (1989), and mouse pontins (MOP) (shown in Craig et al., *J. Bio;. Chem.*, Vol. 264, pp. 9682-9689 (1989), Miyazaki et al., *Nucleic Acids Res.*, Vol. 17, pp. 3298-3298 (1989), and Patarca et al., *J. Exp. Med.*, Vol. 170, pp. 145-161 (1989)). Identity was also established with human lactopontin (not illustrated) (shown in Senger et al., *Biochem. Biophys. Acta*, Vol. 996, pp. 43-48 (1989)). The amino acid sequences of the four osteopontins shown start with position 19 of the precursors and extend to residue 62 (residue 61 for MOP). With the exception of an indeterminate residue 25, the entire N-terminal sequence from residue 2 to 30 of HUP isolated from a second individual was identical to that shown. The last 5 of the 7 amino acids in the N-terminus of human lactopontin are identical to the first 5 amino acids of HUP. The last 4 amino acids (Asn-Ala-Val-Ser) of the HUP sequence are deleted in one of the isoforms encoded by mRNA from human bone, decidua, Young et al., *Genomics*, Vol. 7, pp. 491-502 (1990), and kidney.

The amino acid composition determined for human uropontin, shown in Table 1, includes a very high percentage of aspartic acid residues and corresponds to the distribution of amino acids in human osteopontin. The composition was determined using standard acid hydrolysis and chromatographic techniques, as decribed in Fisher et al., *J. Biol. Chem.*, Vol. 262, pp. 9702-9708 (1987) and Przysiecki et al., *Proc. Natl. Acad. Sci. USA*, Vol. 84, pp. 7858-7860 (1987). Uropontin, however, is quite distinct from nephrocalcin, another protein inhibitor of crystal growth. Nakagawa et al., *J. Biol. Chem.*, Vol. 258, pp. 12594-12600 (1983). The amino acid composition and molecular weights of the two proteins differ substantially, and none of the glutamic acid residues in uropontin are γ-carboxylated as they are in nephrocalcin, osteocalcin and other vitamin K-dependent proteins. The amino acid and nucleotide sequences of nephrocalcin are not yet known. Furthermore, in contrast to TH and coagulation proteins with calcium-binding epidermal growth factor-like domains, Przysiecki et al., *Proc. Natl. Acad. Sci. USA*, Vol. 84, pp. 7858-7860 (1987), none of the aspartic acid and asparagine residues in uropontin were β-hydroxylated, a finding consistent with the lack of epidermal growth factor-like domains in pontin sequences. The overall amino acid composition of proteins extracted from calcium oxalate stones demonstrates a striking preponderance of acidic amino acids and more closely resembles uropontin than nephrocalcin. Lian et al., *J. Clin. Invest.*, Vol. 59, pp. 1151-1157 (1977), Spector et al., *Invest. Urol.*, Vol. 13, pp. 387-389 (1976), and Nakagawa et al., *J. Clin. Invest.*, Vol. 79, pp. 1782-1787 (1987).

Figure 4:
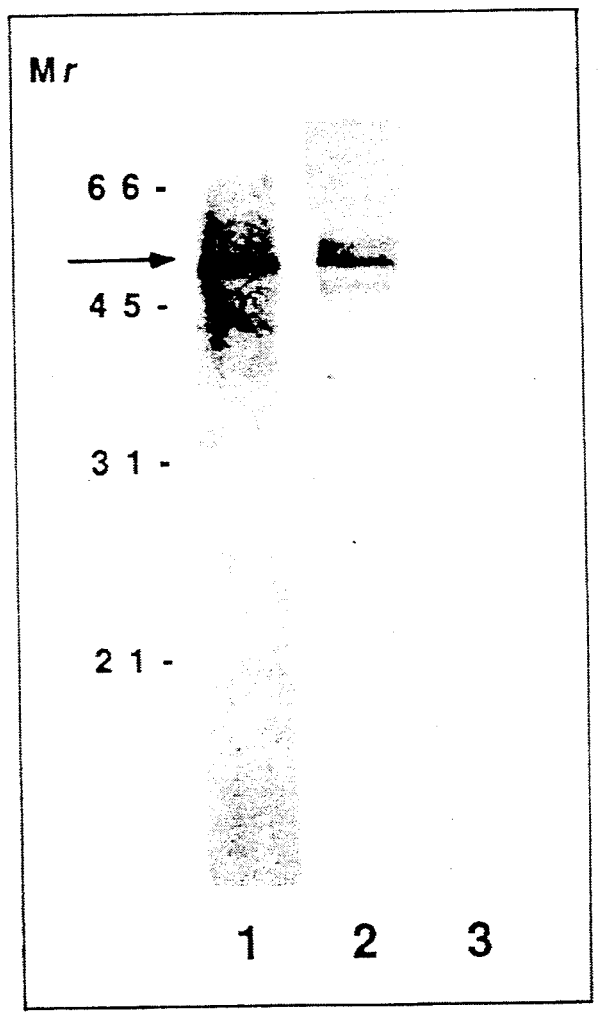
FIG. 4 shows a 16% SDS-PAGE of the uropontin protein of the present invention purified by immunoaffinity chromatography using ZH2 beads. The position of migration of molecular weight markers $\times 10^3$ is shown on the left. Lanes 1 and 2 contain 6 μg samples of uropontin protein per lane and lane 3 contains 6 μg of DEAE batch eluate. Lane 1 was stained with silver. Lanes 2 and 3 are Western blots that used monoclonal antibody ZH2 for detection.

The migration of uropontin on SDS-PAGE varied according to the gel composition. The major band detected by Silver staining and in Western blots migrated to $M_r \sim 50,000$ on 16% gels (FIG. 4) and at $M_r \sim 72,000$ in 5-18% gradient gels. This unusual pattern of migration is very similar to the behavior reported previously for rat osteopontin. Prince et al., *J. Biol. Chem.*, Vol. 262, pp. 2900-2907 (1987), Kubota et al., *Biochem. Biophys. Res. Cumm.*, Vol. 162, pp. 1453-1459 (1989). Human osteopontin migrates at $M_r \sim 80,000$ on 4-20% gels, Fisher et al., J. Biol. Chem., Vol. 262, pp. 9702-9708 (1987), while lactopontin migrates at $M_r \sim 75,000$ in 10% gels, Senger et al., Biochem. Biophys. Acta, Vol. 996, pp. 43-48 (1989).

Example 5

Gene Cloning

To clone the gene encoding the uropontin protein of the invention, an adult human kidney λ gt10 cDNA library (purchased from Clontech, in California) was screened using two oligonucleotide probes having the following nucleotide sequences.

Probe 1
    5'-CTGATTCTGGAAGTTCTGAGGA-3'

Probe 2
    5'-AGATTCTGCTTCTGAGATGGGT-CAGG-3'

Probe 1 corresponds to nucleotides 132-153 of the nucleotide sequence of the osteopontin gene, as published in Kiefer et al., Nucleic Acids Res., Vol. 17, pp. 3306-3308 (1989) (hereinafter referred to as "Kiefer"), and to amino acids 4-11 (from the N-terminus) of SEQ ID NO 1 shown herein. Probe 2 corresponds to nucleotides 203-228 of the osteopontin gene published in Kiefer, and to amino acids 28-36 (from the N-terminus) of SEQ ID NO 1 shown herein. About 250,000 clones were initially screened with $^{32}$P-labeled oligonucleotide and 40 positives were identified. Three of these positives were subcloned, the DNA of these clones was amplified by PCR using λ gt10 forward and reverse primers and ligated into pUC19, and DNA minipreps containing inserts were sequenced using the dideoxy method and $^{35}$S-dATP. To complete the sequencing, two additional oligonucleotide primers having the following sequences were employed.

Primer 1 5'-GAAAGCCATGACCACATGGA-3'

Primer 2
    5'-TTGACCTCAGAAGATG(A,C)ACT-3'

Primer 1 corresponds to nucleotides 305-324 of the osteopontin gene published in Kiefer, and to amino acids 62-68 (from the N-terminus) of SEQ ID NO 1 shown herein. Primer 2 is an antisense oligonucleotide which corresponds to nucleotides 988-1007 of the osteopontin gene published in Kiefer, and to amino acids 289-295 (plus two nucleotides from the codon triplet for amino acid 296) (from the N-terminus) of SEQ ID NO 1 shown herein.

Sequencing carried out on two of the three clones revealed identity to the published nucleotide sequence of human osteopontin, as shown in Kiefer. The sequence of the third clone was exactly identical to the sequence of the coding region shown in Young et al., Genomics, Vol. 7, pp. 491-502 (1990), a sequence which differs from the sequence in Kiefer by the deletion of nucleotides 243-284 of the Kiefer sequence.

TABLE 1

| Amino Acid | Amino Acid Composition (Residues/1000) | | | |
|---|---|---|---|---|
| | Uropontin* | Osteopontin + | ± | Nephrocalcin § |
| CYSTINE | 0 | ND¶ | 0 | 17 |
| ASN + ASP | 207 | 223 | 201 | 106 |
| MET | 7 | ND | 13 | 6 |
| THR | 66 | 40 | 47 | 88 |
| SER | 162 | 122 | 141 | 97 |
| GLU + GLN | 140 | 176 | 138 | 122 |
| PRO | 55 | 76 | 50 | 59 |
| GLY | 69 | 25 | 20 | 108 |
| ALA | 52 | 55 | 47 | 76 |
| VAL | 46 | 42 | 60 | 64 |
| ILE | 15 | 23 | 23 | 24 |
| LEU | 47 | 60 | 54 | 63 |
| TYR | 26 | 9 | 27 | 10 |
| PHE | 16 | 8 | 23 | 31 |
| HIS | 36 | 46 | 54 | 20 |
| LYS | 39 | 64 | 64 | 36 |
| ARG | 17 | 28 | 30 | 41 |
| TRYP | ND | ND | 7 | 9 |
| GLA # | 0 | ND | ND | 20 |

*uropontin isolated from human urine.
+ osteopontin isolated from human bone.
± human osteopontin predicted by cDNA for a mature protein sequence of 298 amino acids. This sequence predicts that 164 of the 201 (Asp + Asn) residues/1000 are aspartic acid and that 103 of the 138 (Glu + Gln) residues/1000 are glutamic acid (12)
§ nephrocalcin isolated from human urine.
¶ ND - not done.
γ-carboxyglutamic acid. In contrast to uropontin, other proteins also present in the main inhibitory peak contained both GLA and β-hydroxyasparagine.

Various modifications of the invention in addition to those shown and described herein will be apparent to those skilled in the art from the foregoing description. Such modifications are also intended to fall within the scope of the appended claims.

What is claimed is:

1. A composition for treating kidney stone disease comprising an amount of a peptide effective for treating kidney stone disease consisting of the peptide of SEQ ID NO 4, natural genetic variants thereof, or active portions thereof, in combination with a pharmaceutically acceptable carrier or diluent.

2. A composition of claim 1 wherein the peptide is the peptide of SEQ ID NO 4.

3. A diagnostic kit comprising a peptide consisting of the peptide of SEQ ID NO 2 or natural genetic variants thereof, and a monoclonal or polyclonal antibody to that peptide, in combination with conventional diagnostic kit components.

4. A diagnostic kit of claim 3 wherein the peptide is the peptide of SEQ ID NO 2.

5. A diagnostic kit comprising a peptide consisting of the peptide of SEQ ID NO 3 or natural genetic variants thereof, and a monoclonal or polyclonal antibody to that peptide, in combination with conventional diagnostic kit components.

6. A diagnostic kit of claim 5 wherein the peptide is the peptide of SEQ ID NO 3.

7. A diagnostic kit comprising a peptide consisting of the peptide of SEQ ID NO 4 or natural genetic variants thereof, and a monoclonal or polyclonal antibody to that peptide, in combination with conventional diagnostic kit components.

8. A diagnostic kit of claim 7 wherein the peptide is the peptide of SEQ ID NO 4.

9. A composition of claim 1 wherein the active portion is the peptide of SEQ ID NO 2.

10. A composition of claim 1 wherein the active portion is the peptide of SEQ ID NO 3.

* * * * *

UNITED STATES PATENT AND TRADEMARK OFFICE
CERTIFICATE OF CORRECTION

PATENT NO. : 5,304,496
DATED : April 19, 1994
INVENTOR(S) : Hoyer et al

It is certified that error appears in the above-indentified patent and that said Letters Patent is hereby corrected as shown below:

Col. 1, line 67, after "thereto" delete the period "." and insert a comma --,--

Col. 7, line 56, "TM" should be superscript

Col. 7, line 58, "TM" should be superscript

Col. 7, line 61, "press" should be --Press--

Col. 10, line 31, following "Example 1" insert the title --Protein Fractionation--

Col. 11, line 32, "With" should be lower case --with--

Col. 11, line 58, "Ma." should be --ME--

Col. 14, line 7, "Bio;." should be --Biol.--

Col. 14, line 60, after "tected" the next line starting with "by" should follow immediately thereafter Signed and Sealed this Twenty-second Day of August, 1995

Attest:

BRUCE LEHMAN

Attesting Officer

Commissioner of Patents and Trademarks

SEQUENCE LISTING ( 1 ) GENERAL INFORMATION:

( i i i ) NUMBER OF SEQUENCES: 5

( 2 ) INFORMATION FOR SEQ ID NO: 1:

( i ) SEQUENCE CHARACTERISTICS:
        ( A ) LENGTH: 296 amino acids
        ( B ) TYPE: amino acid
        ( D ) TOPOLOGY: linear ( x i ) SEQUENCE DESCRIPTION: SEQ ID NO: 1:

Val-Lys-Gln-Ala-Asp-Ser-Gly-Ser-Ser-Glu-Glu-Lys-Gln-Leu-Tyr-
1               5                   10                  15

Asn-Lys-Tyr-Pro-Asp-Ala-Val-Ala-Thr-Trp-Leu-Asn-Pro-Asp-Pro-
            20                  25                  30

Ser-Gln-Lys-Gln-Asn-Leu-Leu-Ala-Pro-Gln-Asn-Ala-Val-Ser-Ser-

```
                    35                          40                            45
Glu-Glu-Thr-Asn-Asp-Phe-Lys-Gln-Glu-Thr-Leu-Pro-Ser-Lys-Ser-
                    50                          55                            60
Asn-Glu-Ser-His-Asp-His-Met-Asp-Asp-Met-Asp-Asp-Glu-Asp-Asp-
                    65                          70                            75
Asp-Asp-His-Val-Asp-Ser-Gln-Asp-Ser-Ile-Asp-Ser-Asn-Asp-Ser-
                    80                          85                            90
Asp-Asp-Val-Asp-Asp-Thr-Asp-Asp-Ser-His-Gln-Ser-Asp-Glu-Ser-
                    95                         100                           105
His-His-Ser-Asp-Glu-Ser-Asp-Glu-Leu-Val-Thr-Asp-Phe-Pro-Thr-
                   110                         115                           120
Asp-Leu-Pro-Ala-Thr-Glu-Val-Phe-Thr-Pro-Val-Val-Pro-Thr-Val-
                   125                         130                           135
Asp-Thr-Tyr-Asp-Gly-Arg-Gly-Asp-Ser-Val-Val-Tyr-Gly-Leu-Arg-
                   140                         145                           150
Ser-Lys-Ser-Lys-Lys-Phe-Arg-Arg-Pro-Asp-Ile-Gln-Tyr-Pro-Asp-
                   155                         160                           165
Ala-Thr-Asp-Glu-Asp-Ile-Thr-Ser-His-Met-Glu-Ser-Glu-Glu-Leu-
                   170                         175                           180
Asn-Gly-Ala-Tyr-Lys-Ala-Ile-Pro-Val-Ala-Gln-Asp-Leu-Asn-Ala-
                   185                         190                           195
Pro-Ser-Asp-Trp-Asp-Ser-Arg-Gly-Lys-Asp-Ser-Tyr-Glu-Thr-Ser-
                   200                         205                           210
Gln-Leu-Asp-Asp-Gln-Ser-Ala-Glu-Thr-His-Ser-His-Lys-Gln-Ser-
                   215                         220                           225
Arg-Leu-Tyr-Lys-Arg-Lys-Ala-Asn-Asp-Glu-Ser-Asn-Glu-His-Ser-
                   230                         235                           240
Asp-Val-Ile-Asp-Ser-Gln-Glu-Leu-Ser-Lys-Val-Ser-Arg-Glu-Phe-
                   245                         250                           255
His-Ser-His-Glu-Phe-His-Ser-His-Glu-Asp-Met-Leu-Val-Val-Asp-
                   260                         265                           270
Pro-Lys-Ser-Lys-Glu-Glu-Asp-Lys-His-Leu-Lys-Phe-Arg-Ile-Ser-
                   275                         280                           285
His-Glu-Leu-Asp-Ser-Ala-Ser-Ser-Glu-Val-Asn
                   290                         295
```

( 2 ) INFORMATION FOR SEQ ID NO: 2:

( i ) SEQUENCE CHARACTERISTICS:
        ( A ) LENGTH: 26 amino acids
        ( B ) TYPE: amino acid
        ( D ) TOPOLOGY: linear ( x i ) SEQUENCE DESCRIPTION: SEQ ID NO: 2:

```
His-Asp-His-Met-Asp-Asp-Met-Asp-Asp-Glu-Asp-Asp-Asp-Asp-His-
1                   5                          10                            15
Val-Asp-Ser-Gln-Asp-Ser-Ile-Asp-Ser-Asn-Asp
                    20                         25
```

( 2 ) INFORMATION FOR SEQ ID NO: 2:

( i ) SEQUENCE CHARACTERISTICS:
        ( A ) LENGTH: 14 amino acids
        ( B ) TYPE: amino acid
        ( D ) TOPOLOGY: linear ( x i ) SEQUENCE DESCRIPTION: SEQ ID NO: 3:

```
Asn-Asp-Ser-Asp-Asp-Val-Asp-Asp-Thr-Asp-Asp-Ser-His-Gln
1                   5                          10
```

5,304,496

19

-continued ( 2 ) INFORMATION FOR SEQ ID NO: 4:

( i ) SEQUENCE CHARACTERISTICS:
        ( A ) LENGTH: 38 amino acids
        ( B ) TYPE: amino acid
        ( D ) TOPOLOGY: linear ( x i ) SEQUENCE DESCRIPTION: SEQ ID NO: 4:

His-Asp-His-Met-Asp-Asp-Met-Asp-Asp-Glu-Asp-Asp-Asp-Asp-His-
1      5            10            15

Val-Asp-Ser-Gln-Asp-Ser-Ile-Asp-Ser-Asn-Asp-Ser-Asp-Asp-Val-
    20           25          30

Asp-Asp-Thr-Asp-Asp-Ser-His-Gln
    35

( 2 ) INFORMATION FOR SEQ ID NO: 5:

( i ) SEQUENCE CHARACTERISTICS:
        ( A ) LENGTH: 282 amino acids
        ( B ) TYPE: amino acid
        ( D ) TOPOLOGY: linear ( x i ) SEQUENCE DESCRIPTION: SEQ ID NO: 5:

Val-Lys-Gln-Ala-Asp-Ser-Gly-Ser-Ser-Glu-Glu-Lys-Gln-Leu-Tyr-
1      5            10            15

Asn-Lys-Tyr-Pro-Asp-Ala-Val-Ala-Thr-Trp-Leu-Asn-Pro-Asp-Pro-
    20           25          30

Ser-Gln-Lys-Gln-Asn-Leu-Leu-Ala-Pro-Gln-Thr-Leu-Pro-Ser-Lys-
    35           40          45

Ser-Asn-Glu-Ser-His-Asp-His-His-Met-Asp-Asp-Met-Asp-Glu-Asp-
    50           55          60

Asp-Asp-Asp-His-Val-Asp-Ser-Gln-Asp-Ser-Ile-Asp-Ser-Asn-Asp-
    65           70          75

Ser-Asp-Asp-Val-Asp-Asp-Thr-Asp-Asp-Ser-His-Gln-Ser-Asp-Glu-
    80           85          90

Ser-His-His-Ser-Asp-Glu-Ser-Asp-Glu-Leu-Val-Thr-Asp-Phe-Pro-
    95           100         105

Thr-Asp-Leu-Pro-Ala-Thr-Glu-Val-Phe-Thr-Pro-Val-Val-Pro-Thr-
    110          115         120

Val-Asp-Thr-Tyr-Asp-Gly-Arg-Gly-Asp-Ser-Val-Val-Tyr-Gly-Leu-
    125          130         135

Arg-Ser-Lys-Ser-Lys-Lys-Phe-Arg-Arg-Pro-Asp-Ile-Gln-Tyr-Pro-
    140          145         150

Asp-Ala-Thr-Asp-Glu-Asp-Ile-Thr-Ser-His-Met-Glu-Ser-Glu-Glu-
    155          160         165

Leu-Asn-Gly-Ala-Tyr-Lys-Ala-Ile-Pro-Val-Ala-Gln-Asp-Leu-Asn-
    170          175         180

Ala-Pro-Ser-Asp-Trp-Asp-Ser-Arg-Gly-Lys-Asp-Ser-Tyr-Glu-Thr-
    185          185         195

Ser-Gln-Leu-Asp-Asp-Gln-Ser-Ala-Glu-Thr-His-Ser-His-Lys-Gln-
    200          205         210

Ser-Arg-Leu-Tyr-Lys-Arg-Lys-Ala-Asn-Asp-Glu-Ser-Asn-Glu-His-
    215          220         225

Ser-Asp-Val-Ile-Asp-Ser-Gln-Glu-Leu-Ser-Lys-Val-Ser-Arg-Glu-
    230          235         240

Phe-His-Ser-His-Glu-Phe-His-Ser-His-Glu-Asp-Met-Leu-Val-Val-
    245          250         255

Asp-Pro-Lys-Ser-Lys-Glu-Glu-Asp-Lys-His-Leu-Lys-Phe-Arg-Ile-
    260          265         270

Ser-His-Glu-Leu-Asp-Ser-Ala-Ser-Ser-Glu-Val-Asn
275                 280